(12) United States Patent
Letovsky

(10) Patent No.: US 8,927,264 B2
(45) Date of Patent: Jan. 6, 2015

(54) ELECTRO MEDICAL TOOL OPTIMIZATION SYSTEM

(71) Applicant: Howard Letovsky, Willits, CA (US)

(72) Inventor: Howard Letovsky, Willits, CA (US)

( * ) Notice: Subject to any disclaimer, the term of this patent is extended or adjusted under 35 U.S.C. 154(b) by 51 days.

(21) Appl. No.: 13/868,330

(22) Filed: Apr. 23, 2013

(65) Prior Publication Data

US 2014/0315286 A1 Oct. 23, 2014

(51) Int. Cl.
*C12N 1/00* (2006.01)
*C12M 3/00* (2006.01)
*C12M 1/34* (2006.01)
*C12M 1/42* (2006.01)
*G01N 33/483* (2006.01)

(52) U.S. Cl.
CPC ........... *C12M 35/02* (2013.01); *G01N 33/4833* (2013.01)
USPC .................. 435/288.7; 435/283.1; 435/287.1; 435/287.2

(58) Field of Classification Search
CPC .......... G01N 21/6428; G01N 21/6452; C12M 1/3446
USPC ............................................. 435/283.1–309.4
See application file for complete search history.

(56) References Cited

U.S. PATENT DOCUMENTS

2005/0118705 A1* 6/2005 Rabbitt et al. ............. 435/287.1
2006/0121446 A1* 6/2006 Abassi et al. ...................... 435/4
2007/0238092 A1* 10/2007 Rubesa .............................. 435/4
2010/0015682 A1* 1/2010 Sasaki et al. ................ 435/173.9
2012/0295253 A1* 11/2012 Abassi et al. ................... 435/6.1

* cited by examiner

*Primary Examiner* — Nathan Bowers
*Assistant Examiner* — Lydia Edwards

(57) ABSTRACT

Methods and apparatus are disclosed herein to improve on and expand the range of electrical and electromagnetic frequencies used in therapeutic electro medical devices. The present invention uses electrical and electromagnetic frequency generators and detectors integrated with a live cell imaging system that provides feedback to the frequency generators using data derived from said imaging system.

16 Claims, 8 Drawing Sheets

ELECTRO MEDICAL TOOL OPTIMIZATION SYSTEM

FIELD OF THE INVENTION

The present invention relates to methods and apparatus intended to accelerate the healing rates of hard and soft human or animal tissues and promote regeneration of damaged organs using electrical and electromagnetic stimulation.

BACKGROUND OF THE INVENTION

In every arena of medical practice, the healing of tissues is the primary problem that must be dealt with. Trauma induced contusions; abrasions, organ failures, and bone damage are medical issues dealt with by the millions daily. Typical medical approaches to trauma include stitches, bandages, casts, as well as simple and complex mechanical restructuring, then letting the body takes its natural healing course. Disease is rampant in current society as evidenced by the flood of "pills" offered on television and pharmacy shelves. The bulk of these products rarely heal the tissues themselves, but seek to neutralize the symptoms resulting in side effects that are often worse than the disease itself. Non-invasive tissue regeneration tools that have no side effects are needed.

Key prior art patents that relate to the present invention are presented herein with summaries of their abstracts. The Yoshida et al. U.S. Pat. No. 5,922,209 describes a process for deactivating or destroying microorganisms by applying electrical energy to a microorganism through a liquid, gas or solid having electrical energy to cause an increase in an electric charge in excess of the limit of intracellular and extracellular electrostatic capacity possessed by the microorganism, which in turn results in an irreversible change in the microorganism cells and/or explosively destroys the border membrane of the microorganism cells.

Chang's U.S. Pat. No. 5,304,486 discloses a method of and apparatus for cell portion and cell fusion using radiofrequency electrical pulses. The method can be used to fuse or porate a variety of cells including animal cells, human cells, plant cells, protoplasts, erythrocyte ghosts, liposomes, vesicles, bacteria and yeasts. The method can also be used to produce new biological species, to make hybridoma cells which produce animal or human monoclonal antibodies and to insert therapeutic genes into human cells which can be transplanted back into the human body to cure genetic diseases.

The Saban, et al. U.S. Pat. No. 6,790,341 provides microband electrode array sensors for detecting the presence and measuring the concentration of analytes in a sample. The microband electrodes of the invention have both a width and thickness of microscopic dimensions. Preferably the width and thickness of the microband electrodes are less than the diffusion length of the analyte(s) of interest. The electrodes are separated by a gap insulating material that is large enough that the diffusion layers of the electrodes do not overlap such that there is no interference and the currents at the electrodes are additive.

Edwards, et al. U.S. Pat. No. 5,472,441 discloses a device for treating body tissues containing cancerous cells or non-malignant tumors with RF ablation, alone or in combination with systemic or localized chemotherapy.

The Harris, et al. U.S. Pat. No. 6,400,487 teaches methods and apparatus for screening large numbers of chemical compounds and performing a wide variety of fluorescent assays, including live cell assays. The methods utilize a laser linescan confocal microscope with high speed, high resolution and multi-wavelength capabilities and real time data-processing.

Chang's U.S. Pat. No. 8,278,629 discloses live-cell observation equipment for a non light-transmitting microscope to study temperature-dependent events and method thereof.

Hofmann's U.S. Pat. No. 4,561,961 describes a cooled microscope slide and electrode apparatus for use in live cell fusion system employing tubular electrodes so fluid may be pumped through the electrodes to dissipate heat to enhance the yield of viable hybrids. An alternate embodiment sandwiches a gasket and parallel tubular electrodes between glass slides to permit cell fusion in a closed sterile environment.

This inventor's own Letovsky U.S. Pat. No. 6,825,792 discloses a frequency based missile detection and neutralization system that uses some similar components and creates some similar effects in non-organic compounds as the present invention does in organic compounds. This inventor's published patent application Letovsky 20110001064—as well as the parent patent from which it is a divisional—discloses aspects related to the present invention without including the camera image data to waveform generator feedback loop, the variable color source, direct contact electrical to cell system, and non contact electromagnetic frequency application components specification provided herein which are necessary to make the present invention function as intended.

The present invention is the result of many years of research into electrical and electromagnetic stimulation of cells to promote accelerated healing, the potential reactivation of stem cell activity, hard and soft tissue regeneration, as well as immune system stimulation to combat cancer, heart disease, and general autoimmune dysfunction.

SUMMARY OF THE INVENTION

The primary objective of the present invention is to expand the catalog of frequencies used in the electro medical tool industry by providing a research toolset to observe and affect live cells and live tissue samples in real time with high resolution, high contrast live cell imaging analysis under both direct electrical contact and non-contact electromagnetic wave stimulation. The present invention may provide better frequency choices to enhance the healing processes in virtually every cell type in human and other animal bodies.

Another objective of the present invention is to define electrical and electromagnetic frequencies that may promote the enhanced uptake of beneficial drugs, vitamin and mineral compounds in a living organism.

Radiation from the sun, space, and the atmosphere, as well as brainwaves, bioelectric signals, water, and food chemistry drive living cell metabolic processes. When an organism's metabolism is out of balance with its baseline genetic programming, disease is the result. The electro medical tool industry uses electrical and electromagnetic frequencies from several hertz to light waves to assist in this metabolic rebalancing. The industry is now into its second century of evolution having begun largely in Eastern Europe.

Russian documentation detailing electrical physiotherapies goes from present day back to the mid 1800s, and incorporates sound, ultrasound, radio frequencies and specific light frequencies. Japanese carbon arc light healing tools date back to the second world war—healing radiation burn victims after atomic bombs were dropped on Hiroshima and Nagasaki. These highly specific carbon compounds create intense light outputs designed to reproduce specific combinations of light wave frequencies to expedite the body's natural healing processes. Clinical documentation of the effectiveness of this technology is very broad.

Scientists at the University of Alberta in Canada have successfully regenerated teeth from the root up—by the application of specifically configured 1.5 megahertz pulses. Electrical bone growth stimulation is now common throughout the world using specifically configured frequencies at 76.4 hertz, 40 kilohertz, and 1.5 megahertz to increase the speed of bone growth after a fracture or surgery.

Therapeutic "cold" lasers have been proven to increase cell metabolism, increase collagen synthesis for increased healing of soft tissues, increase osteoblast production for increased healing of bone, increase circulation through increased formation of new capillaries by release of growth factors, increase T-cell production for increased immune function, increase production of neurotransmitters such as endorphins, serotonin, ACTH etc., and increase chronic pain threshold through decreased C-fiber activity.

Cancer cure rates with chemotherapy and radiation—though increasing significantly in certain types of cancers—are still lacking in long term cancer cell elimination after decades of research and billions of dollars spent. Electro therapy tools in global research centers are starting to gain traction as being potentially useful for targeting cancer cells while leaving the immune system and neighboring healthy cells undamaged.

In the US, electro medical therapy home use products are now showing up everywhere—mostly "copy catting" each other with a very small number of frequencies used in therapeutic ultrasound, therapeutic lasers, TENS machines, galvanic skin stimulators, frequency specific microcurrent generators, etc. Often, beneficial results of these tools are "hit or miss" with users—yet scores of these product offerings in the market. In general the electro therapy tools available to the public are limited in their accuracy and effectiveness due to a lack of direct testing on live cells both inside and outside living bodies due to a lack of combined observation, analysis, and affectation tools The present invention is designed to fill this need.

All living cells are electrically active. Heart cells grown outside a body in-vitro will all synchronize and beat together even though they are not part of a complete heart. Cells operate and communicate with other cells both electrically and chemically. Live cells can be effected by electric stimulation as in heart pacemakers. Cells also emit electrical frequencies and voltages that can be measured with tools like electroencephalographs and electrocardiographs. Neural tissues generate oscillatory activity in many ways, driven either by mechanisms localized within individual neurons or by interactions between neurons. An electric eel can discharge electrical bursts up to 600 volts at lethal currents.

The present invention integrates wideband frequency generators, transducers, sensors, frequency analyzers, wavelength meters, light power meters, cameras, computers, and computer software to discover "bioactive frequencies" through computer image analysis of the effects of electrical and electromagnetic frequencies on living tissues to promote accelerated healing.

The present invention also incorporates a database with fields and lookup tables populated from tissue and cell reactions data derived from real time image capture and event tracking software that locks, on to cell behavior changes in response to electrical and electromagnetic frequencies applied to the cells. These datasets are continually updated as effects are observed and quantified, and the electrical and electromagnetic frequencies are automatically modified and augmented to accelerate beneficial changes. For example, If a certain frequency clearly speeds up cell division during a frequency sweep, that frequency may be locked in, and harmonics of that frequency at different points in the electromagnetic spectrum may be added with the goal of further accelerating beneficial changes in cell behavior while reducing the electrical power required.

In the present invention, frequencies ranging from DC to x-rays—including sub nanometer resolution monchromated light—are applied to live cell samples for both observation and affectation. Both non contact electromagnetic field generating transducers in close proximity to a live cell sample, and direct electrical application to live cell samples through electrodes fitted to microscope slides are used to apply the frequencies to the cells. The electrode fitted microscope slides may incorporate multiple electrical contact zones to apply voltage and current at various frequencies to live cell samples, read the changes in the impedance of the samples, and read the characteristics of the frequency waves (sine, square, etc.) passing through the samples. There may be a minimum of three contact points per zone—positive in, positive out, and ground—with all zones able to be wired in parallel or dealt with separately. The voltage levels may be quite high—up to 400 volts—but the current may be small—microamp to milliamp levels. Each zone may be 20 by 20 microns or smaller. This may be achieved with clear conductive overlays like cell phone touch screen flexible conductive films affixed to microscope slides.

Impedance matching may be necessary to correctly apply the required frequency and energy level outputs to induce desired results since tissue density and impedance changes with body depth and any electrical or electromagnetic frequency applied. Tissue simulators are used in ultrasound transducer calibration and may also be used in the present invention to set benchmarks for signal amplitude output ratios and impedance matching to account for the differences in signal penetration between a fully functional living body and a sample containing just a few living cells.

A more complete understanding of the present invention, as well as further features and advantages, will be obtained by reference to the following detailed description and drawings. Preferred embodiments of the present invention will be described in the dependent claims.

DETAILED DESCRIPTION OF THE INVENTION

Figure 1:
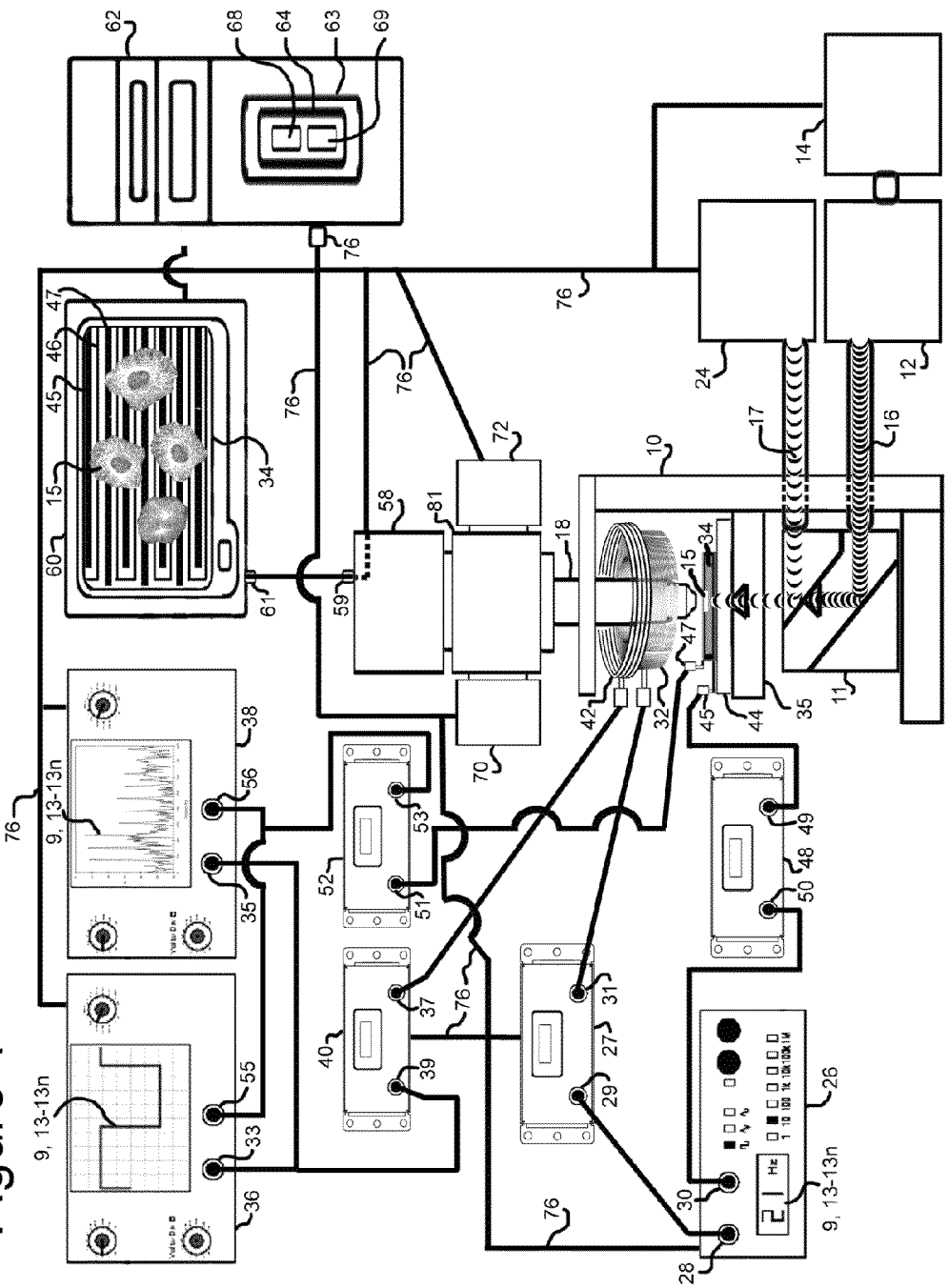
FIG. 1 is a schematic key component diagram illustrating an electro medical tool optimization system per the present invention.

The preferred embodiment of an electro medical tool optimization system in accordance with the present invention per the system flow chart schematic as shown in FIG. 1 may provide the capability to detect a specific live cell 15 anywhere in a live cell sample 34 containing multiple cells, and subsequently apply electrical or electromagnetic signals to a cell sample 34 and modify the behavior of any specific cell 15. Said electrical or electromagnetic signals may be drawn from a frequency range including DC through x-rays. The present invention is designed to effect live cells, observe and collect data on said effects, and use said data to optimize said effects to catalyze a specific cell function modification or neutralization.

The preferred embodiment of an electro medical tool optimization system in accordance with the present invention is shown in FIG. 1 through FIG. 7, and all said Figures with duplicate, expanded, or detailed renderings of specific elements will share the same numbers for said elements. In FIG. 1 specifically, cell sample 34 and cell 15 are represented simultaneously below lens 18 and as part of a screen image in video display 60.

As presented in FIG. 1, the present invention may include a microscope 10, which may be configured with a monochromator 12 capable of splitting a white light source 14 into single nanometer or sub nanometer wavelengths 16 that may range from 200 to 1100 nanometers, but said wavelengths 16 in practice may only be limited by the state of the art in monochromator 12 technology. Monochromator 12 may output any of said wavelengths 16 through any cell 15 in a cell sample 34 and on through a lens 18 of microscope 10.

Monochromator 12 may be operated manually or it may be electrically coupled to computer 62 which is configured with software program 63. Software program 63 may be configured to direct monochromator 12 to provide desired specific wavelengths 16.

Alternatively, software program 63 may be configured to control a variable color light source 24 that is electrically coupled to a computer 62 and capable of outputting any one of millions or billions of colors 17, said colors 17 in practice may only be limited by the state of the art in computer software and variable color light source 24 technology. Source 24 may also be configured to output said colors 17 through any cell 15 in a cell sample 34 and on through a lens 18 of microscope 10. Source 24 may be a video projector, an RGB color laser array, a super continuum laser, or any other variable color emitting light source that derives its color output commands manually by a user or from a software program 63 on a computer 62. A dual beam combiner 11 may also be used to combine and aim the light outputs from monochromator 12 and source 24 through any cell 15.

Figure 3:
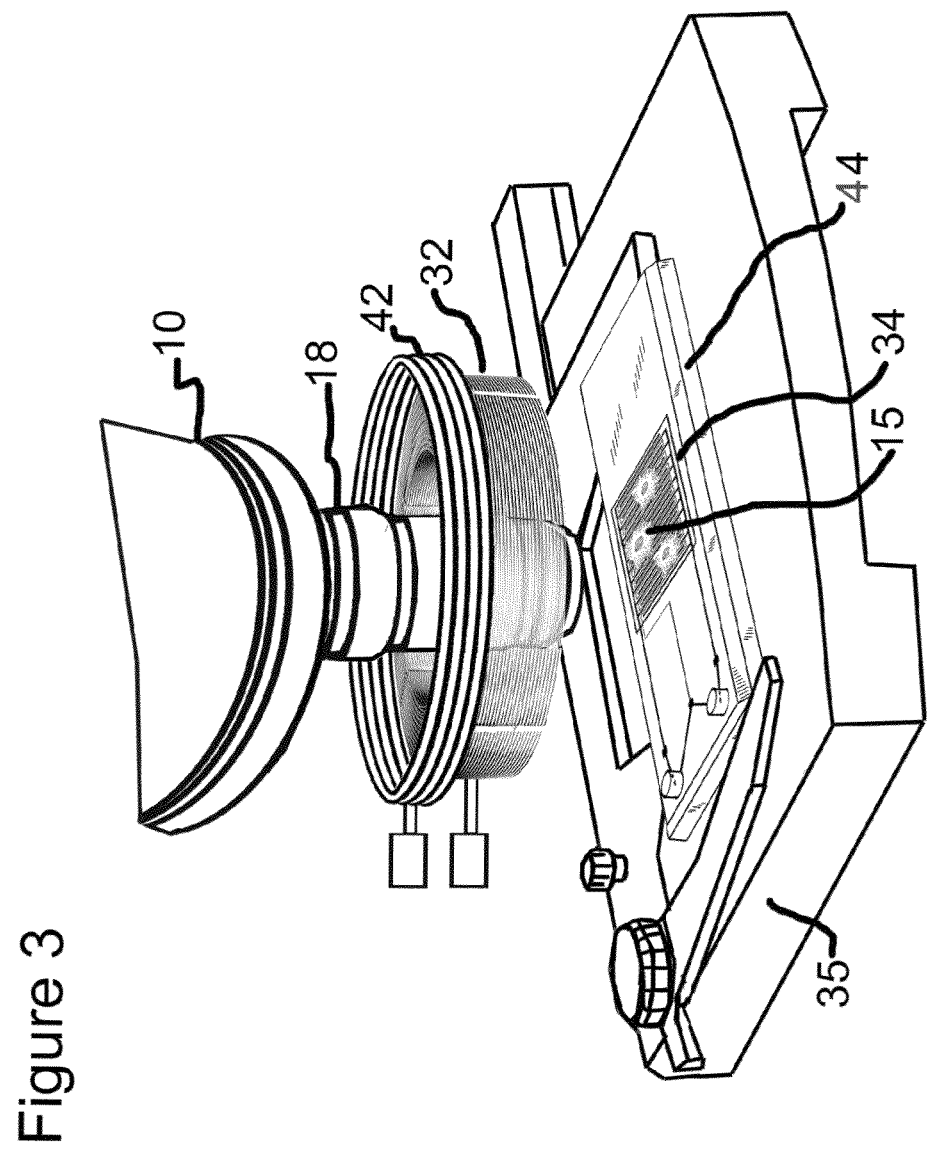
FIG. 3 is a microscope head per the present invention fitted with transmission and pickup coils, as well as a conductive trace fitted slide.
Figure 3A:
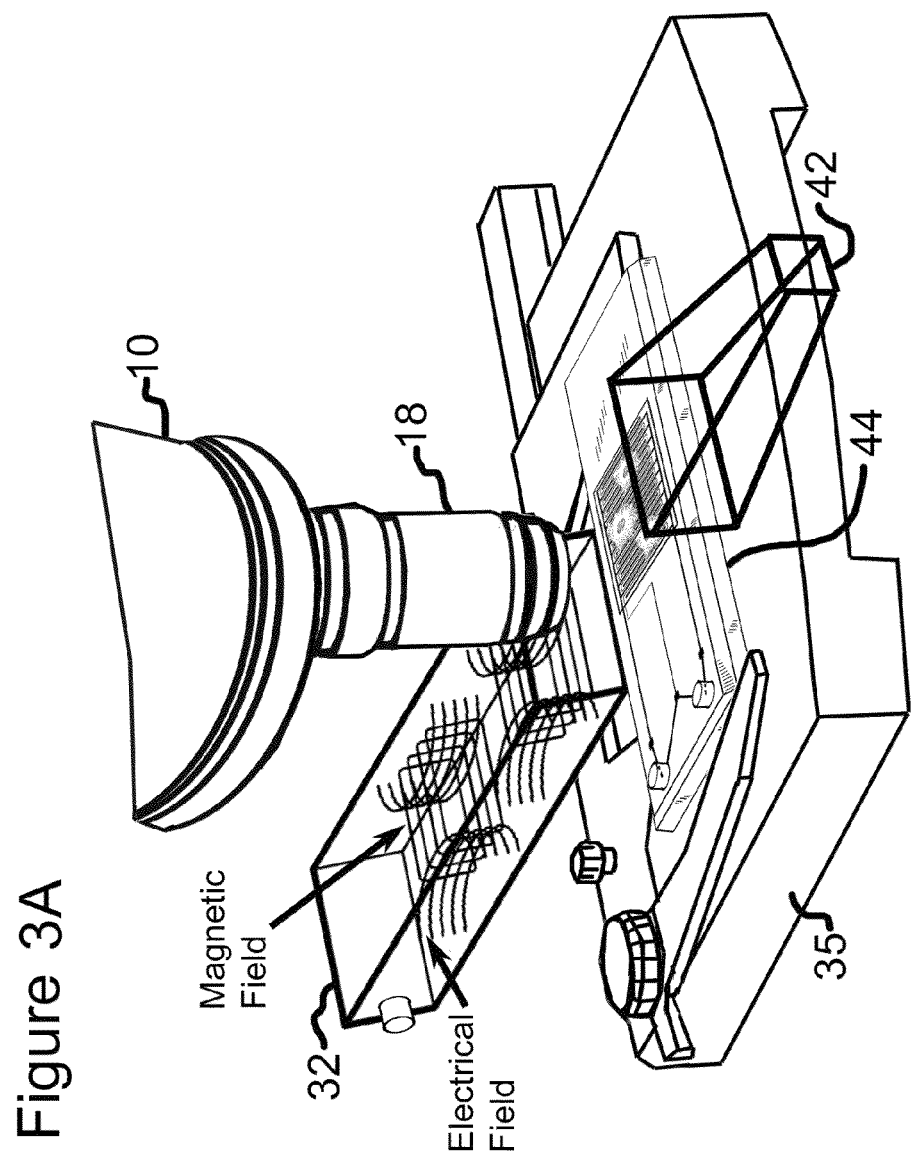
FIG. 3A is a microscope head per the present invention fitted with a waveguide, as well as a conductive trace fitted slide.

A waveform generator 26 with at least two channels of signal outputs 28 and 30, may be electrically coupled to a wideband power amplifier 27 input 29 through waveform generator output 28. Amplifier 27 output 31 may be electrically coupled to an electromagnetic field output transducer 32 which may be mechanically mounted to microscope 10 to surround a microscope lens 18 to induce an electromagnetic field into any cell 15 in cell sample 34 placed on a microscope stage 35. In certain cases, waveform generator 26 may be also be electrically coupled directly to electromagnetic field output transducer 32 through waveform generator output 28 by bypassing amplifier 27. Electromagnetic field output transducer 32 may be single transducer or a plurality of transducers configured to generate an electromagnetic field in response to any waveform 9 provided by waveform generator 26. In certain frequency ranges electromagnetic field output transducer 32 may be a waveguide as shown in FIG. 3A.

Waveform generator 26 may output any standard function generator waveform 9 including but not limited to sine, square, ramp, pulse, noise, DC, as well as a user defined waveform 9 with sweep functionality, variable duty cycle, variable amplitude, and variable frequency range from DC to 300 gigahertz ideally—which is where infrared light frequencies begin. The Anritsu MG3690C with frequency extender options can cover near DC to 500 gigahertz in one box. For the purposes of the present invention said waveform generator 26 frequency range in practice may only be limited by the current state of the art.

Waveform Generator 26 is also connected to computer 62 through instrument interface 76 to allow data transfer and functional control by software program 63. All components presented herein are connected to computer 62 through instrument interface 76 for bidirectional data transfer. These data couplings between computer 62 and all other components described in the present invention may be USB, RS232, Firewire, GPIB, or any other industry standard instrumentation data interface. The electrical signal couplings between all components may be BNC cables or any other industry standard.

Power amplifier 27 should have frequency response equal to waveform generator 26. waveform generator 26 may also have an input 25 which is electrically coupled to computer 62. Electromagnetic field output transducer 32 should have frequency response equal to waveform generator 26.

The input 37 of a wideband amplifier 40 may be electrically coupled to an electromagnetic pickup transducer 42 which may be mechanically mounted concentrically to transducer 32 on microscope 10 such that it can detect any electromagnetic waves that may be applied to the proximity of any cell 15 in cell sample 34 by electromagnetic transducer 32. Amplifier 40 ideally may eliminate any impedance mismatches in pickup transducer 42 as any waveform 9 may be applied to transducer 32 from waveform generator 26 through power amplifier 27. Amplifier 40 may have the same frequency response as amplifier 27. Electromagnetic pickup transducer 42 may be a single transducer or a plurality of transducers configured to sense an electromagnetic field in response to any waveform 9 provided by waveform generator 26. In certain frequency ranges electromagnetic pickup transducer 42 may be a waveguide as shown in FIG. 3A.

An oscilloscope 36 input channel 33 and a spectrum analyzer 38 input channel 35 may be electrically coupled in parallel to the output 39 of amplifier 40. Oscilloscope 36 and spectrum analyzer 38 may have the same frequency response as waveform generator 26 and may be used to insure that any waveform 9 applied to transducer 32 are in fact reaching cell sample 34. Oscilloscope 36 and spectrum analyzer 38 may also be directly electrically connected to transducer 42 and in certain configurations of the present invention by bypassing amplifier 40. Additionally, oscilloscope 36 and spectrum analyzer 38 functions may be incorporated into a single spectrophotometer device.

In the preferred embodiment of the present invention in FIG. 1, waveform generator 26, wideband power amplifier 27, microscope stage 35, wideband amplifier 40, oscilloscope 36, spectrum analyzer 38, wideband power amplifier 48, wideband amplifier 52, camera 58, wavelength meter 70, and optical power meter 72 may all be electrically coupled to computer 62 through industry standard instrumentation interface 76 to allow functional control by software program 63.

Figure 2:
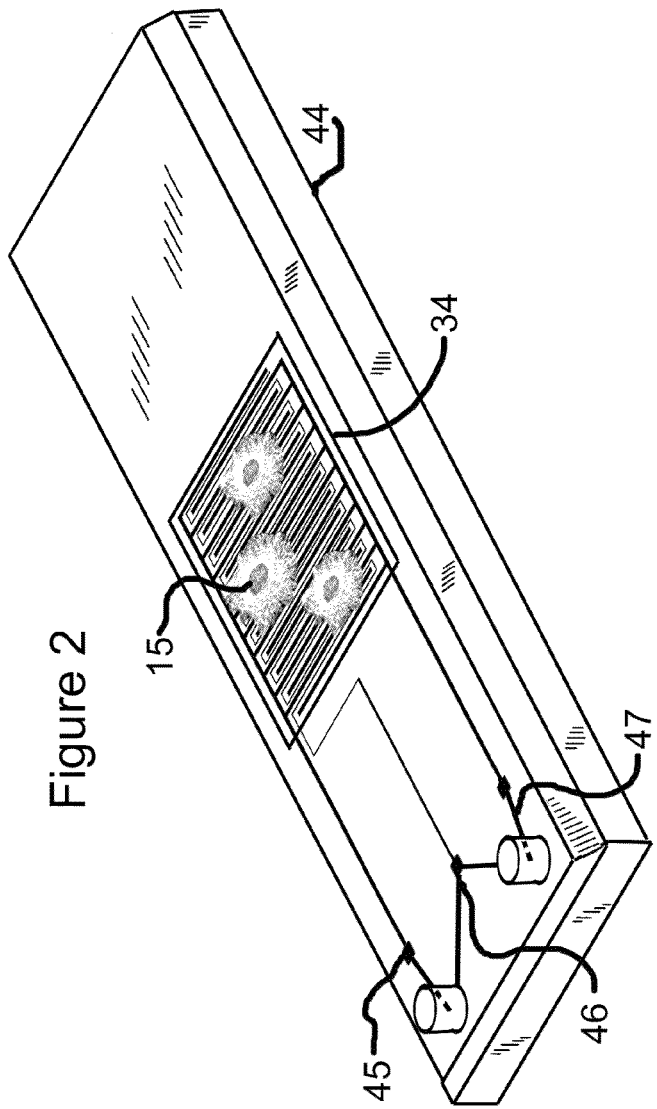
FIG. 2 is a slide per the present invention fitted with conductive traces contacting a cell sample.

As detailed in FIG. 2, cell sample 34 may also be contained on an electrically conductive microscope slide 44. Slide 44 may be configured with a minimum of three electrically conductive traces 45, 46, and 47 configured to make electrical contact with any cell 15 in cell sample 34.

Referring again to FIG. 1, slide 44 and traces 45, 46, and 47 are shown expanded on display 60 to further clarify their configuration. Trace 46 may be the ground connection for input trace 45 and output trace 47. Slide 44 input trace 45 may be electrically connected to wideband power amplifier 48 output 49. Input 50 on amplifier 48 may be electrically connected to output 30 of waveform generator 26. Power amplifier 48 should have frequency response equal to waveform generator 26.

Slide 44 output 47 may be electrically connected to input 51 of a wideband amplifier 52. Amplifier 52 output 53 may be electrically coupled in parallel to oscilloscope 36 second input channel 55 and spectrum analyzer 38 second input channel 56. Amplifier 52 ideally may eliminate impedance mismatches in any cell 15 in a cell sample 34 as any waveform 9 may be applied to traces 45 and 47 from waveform generator 26 through power amplifier 48. Amplifier 52 should have the same frequency response as waveform generator 26.

Camera 58 may be mounted on a beam splitter 81 on said microscope 10 so as to view cell sample 34 through lens 18. A video display 60 input 61 may be coupled to video output 59 of camera 58 to allow a user to monitor any effect of waveform generator 26 waveform 9 on any cell 15 in a cell sample 34. Additionally, video output 59 may be also electrically coupled to computer 62 through instrument interface 76. Software program 63 may be configured to track and map any cell 15 in cell sample 34 and populate database 64 with cell 15 size and cell mechanics data derived from image data provided by camera 58.

Baseline cell behavior information 68 may be included in database 64. Baseline cell behavior information 68 may include typical cell size for a given cell type, rate of mitosis, molecular pathway openings and closings relative to certain chemical compounds, etc. Software program 63 may be configured to detect any cellular behavior alteration 69 from camera 58. Cellular behavior alteration 69 may include any cell 15 behavior deviation from a baseline cell behavior information 68, including such changes as size and shape. Baseline cell behavior information 68 may be refreshed with respect to initial cell 15 size data at the start of every experiment.

Wavelength meter 70 and optical power meter 72 may also-be installed on beam splitter 81 on microscope 10 to log the spectral information of a cell sample 34 before and after application of said waveforms 9 from waveform generator 26. Wavelength meter 70 and optical power meter 72 may be electrically coupled to computer 62 through instrument interface 76 and information they provide may continually populate relevant fields in database 64. Software program 63 may be configured to modify the waveforms 9 in response to any cellular behavior alteration 69 occurring in response to any waveform 9, light wavelength 16, or light color 17. Wavelength meter 70 and optical power meter 72 may have the same frequency response as monochromator 12 and source 24. Wavelength meter 70 and optical power meter 72 may also be a single spectrometer device incorporating the functions of both.

As camera 58 image data updates database 64, cellular behavior alteration 69 data may enable software program 63 to track hundreds of cells in a cell sample 34 simultaneously.

In database 64, each cell 15 location within cell sample 34 on slide 44 may be represented in the x/y/z axes relative to a "zero" point on a three dimensional environment model mapped to the observable area of a microscope slide 44 in database 64 at a resolution of 0.2 microns, or a resolution only limited by current state of the art in optical lens technology.

This type of "object of interest" microscopic targeting and tracking software is now available from an array of software providers.

Each cell 15 initial size may be logged with the same resolution of 0.2 microns, or a resolution only limited by current state of the art in optical lens technology.

Any cellular behavior alteration 69 data may be logged and updated in real time continually updating field data in database 64 as managed by software program 63.

An array of statistical outputs from cellular behavior alteration 69 data may include:
a. real time updated position information of any cell 15 in environmental model 71.
b. acceleration/deceleration of any cell 15 in real time and over time.
c. expansion/contraction of any cell 15 in real time and over time.
d. ambient fluid flow into/out of any cell 15 in real time and over time.

A user of the present invention may initially set waveform generator 26 to sweep a waveform 9 from DC up to the frequency limits of waveform generator 26 at a particular sweep rate not to exceed the image and data acquisition limits of camera 58. When any cellular behavior alteration 69 occurs, the waveform 9 being output at that moment may be locked in by a user or software program 63 and the signal amplitude may be raised or lowered or the pulse width or duty cycle may be altered. Waveform generator 26 may then be directed by a user or software program 63 to add a harmonic 13 of root waveform 9 to waveform 9. Additional harmonics from 13$p$ to 13$n$, as well as wave shape and amplitude alterations may also be tested until no more cellular behavior alteration 69 occurs.

A user may also manually choose to lock-in or sweep through the light wavelength 16 outputs of monochromator 12 and variable color source 24 colors 17. Software program 63 may also be configured to sweep through and lock in any wavelength 16 or colors 17 of light, or combinations of the light outputs of monochromator 12 and variable color source 24 at a particular sweep rate not to exceed the image and data acquisition limits of camera 58.

Figure 6:
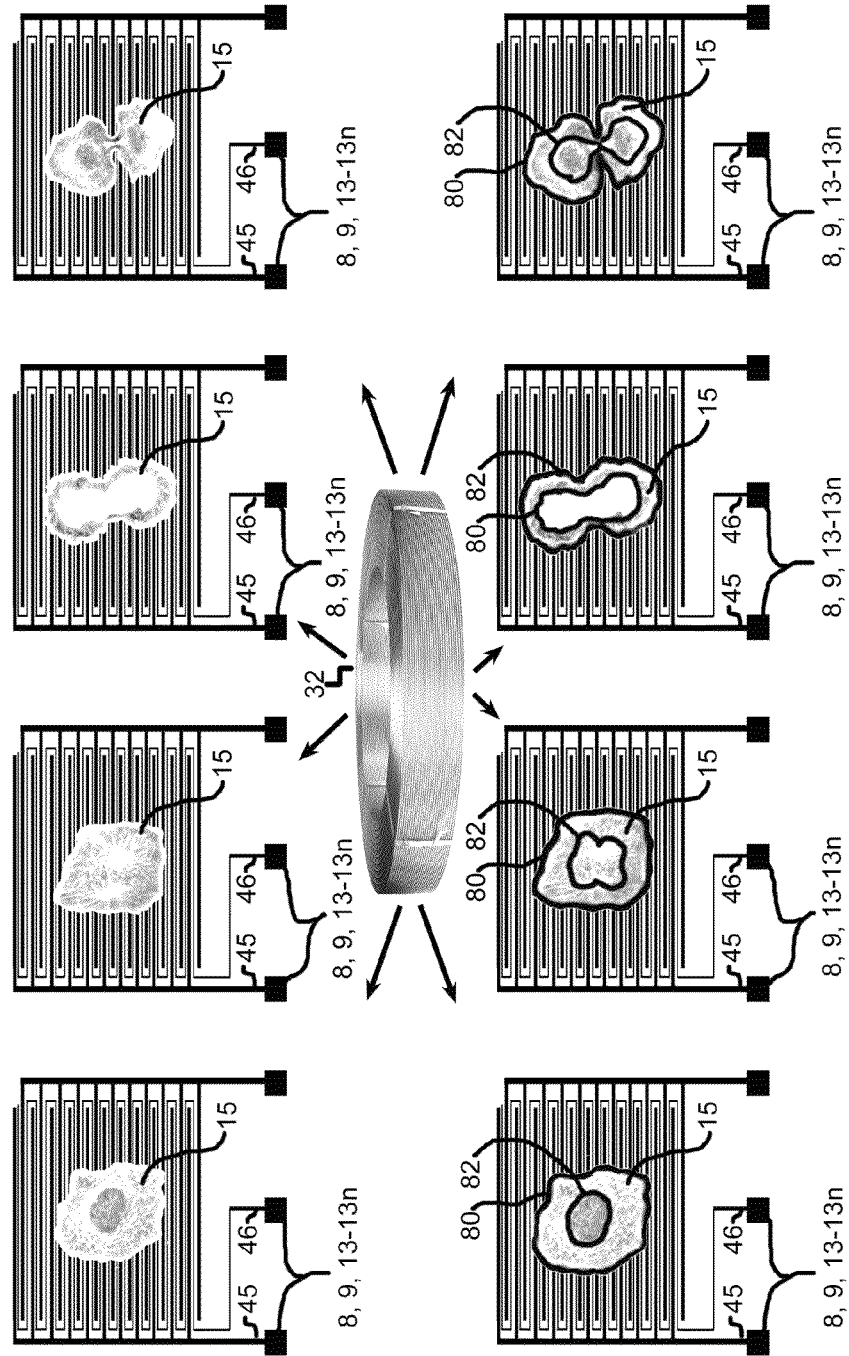
FIG. 6 is a series of simulated accelerated cell changes with cell perimeter and detail mapping per the present invention.

Those frequency waves that are most absorbed by a cell 15 may be considered for the purposes of the present invention as indicated in FIG. 6, resonant frequencies 8 of a cell 15. Said resonant frequencies 8 are a subset of any available waveform 9 and must initially be identified through laboratory experimentation, and are then integrated within database 64 as lookup tables. "Overdriving" the amplitude of said resonant frequencies 8 with respect to a base rate of frequency absorption of a cell 15, said rate data contained in database 64, may affect the electrical conductivity and the chemical and mechanical conditions of a cell 15. These resonant frequencies 8 may then be manipulated and augmented by changes in pulse rate, amplitude, and wave shape, as well as the addition of frequency inversions, harmonics, and dissonances of said resonant frequencies 8 by software program 63 through computer 62 and waveform generator 26. It may be the manipulation of these resonant frequencies 8, combined with other waveforms 9 and one or more of harmonic 13 through 13$n$ combinations that catalyze a cellular behavior alteration 69.

Resonant frequencies 8, combined with other waveforms 9 and harmonic 13 through 13$n$ may be applied to catalyze destruction of a cancerous cell 15 mechanics—initially by altering a single specific structure or behavior within a cell 15, and then outputting and altering additional applied waveforms 9 and harmonic 13 through 13$n$ combinations, which may then propagate state changes in other cell 15 structures and mechanics like a domino effect—possibly allowing an immune system to recognize a cancer cell 15 within a cell sample 34 as an invader and dispatch white blood cells to destroy it For example, if a molecule of a given component may be comprised of ten atomic elements arranged in a particular way, modifying the polarity of the third most abundant atomic element in the molecule may have such a catalyzing effect on a cell 15 mechanics.

Figure 4:
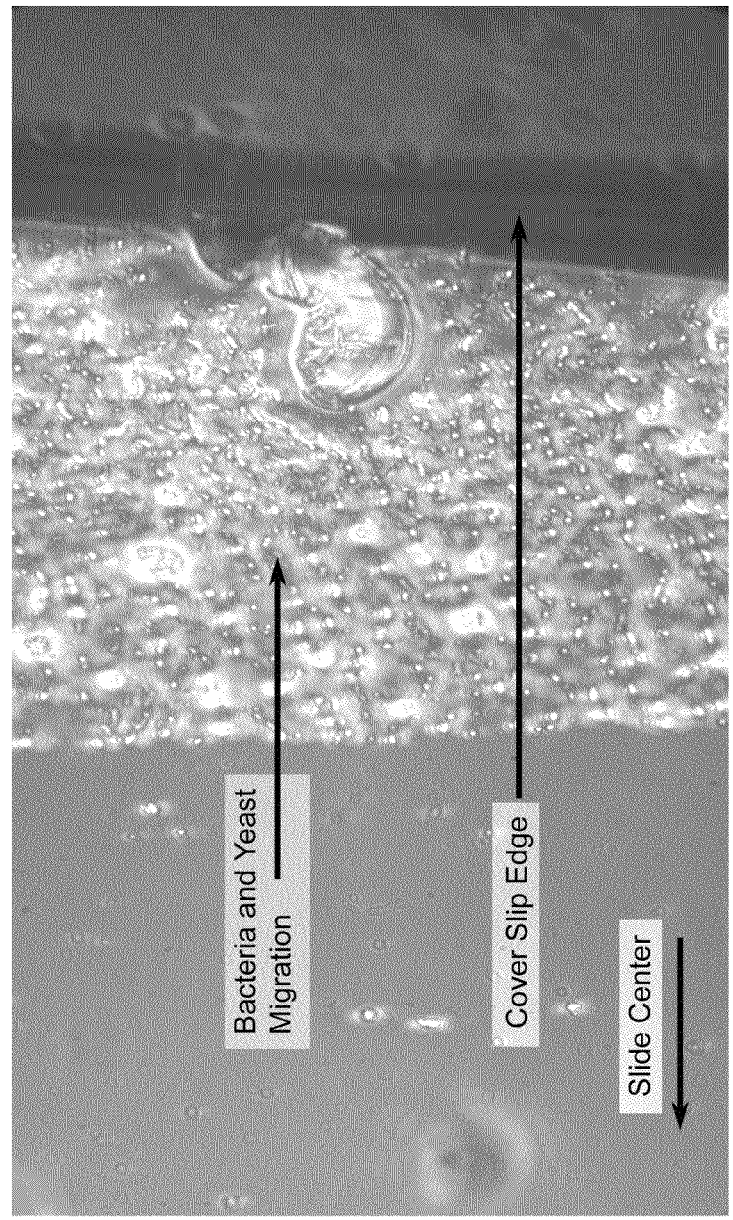
FIG. 4 is a cell sample having been affected by an electromagnetic frequency per the present invention.

Referring now to FIG. 4 which is a photograph from a laboratory experiment using the present invention, sine wave frequencies of 727 hertz were applied to a cell sample 34 consisting of residue from a wine tank. Said cell sample 34 contained many bacteria and yeast cell 15 examples in large numbers. After a few minutes it was observed that almost a cell 15 elements migrated to the cover slip edges of slide 44—leaving the middle of the cover slip area almost empty. This is a simple example of electromagnetic effects on organisms at the microscopic level.

Figure 5:
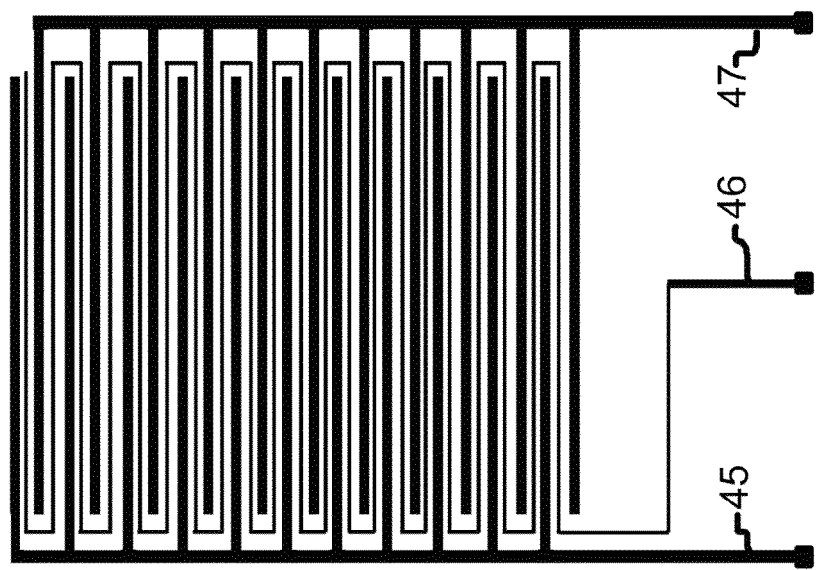
FIG. 5 is a detail of a conductive trace pattern that may be applied to microscope slide per the present invention.

FIG. 5 is one possible trace detail per the present invention that may be rendered on a clear conductive film which may be applied to a glass or polycarbonate microscope slide. Said clear conductive film traces 45, 46, and 47 may be printed or separated by conductivity neutralized areas.

Referring now to FIG. 6, a resonant frequency 8, individually or combined with a waveform 9 and a harmonic 13 through 13n combinations may be applied to a cell 15 through traces 45 and 46 and/or electromagnetic transducer 32 to stimulate a cellular behavior alteration 69 in the form of simulated accelerated mitosis as seen in the series of cell 15 changes illustrated in the top row. In the bottom row of FIG. 6, said cellular behavior alteration 69 may be mapped (by software program 63 in response to image data derived from camera 58 as detailed in FIG. 1) as black outline 80 around the perimeter of cell 15 and black outline 82 around the nucleus 83 of a cell 15. The black arrows indicate electromagnetic waves radiating from electromagnetic transducer 32.

Figure 6A:
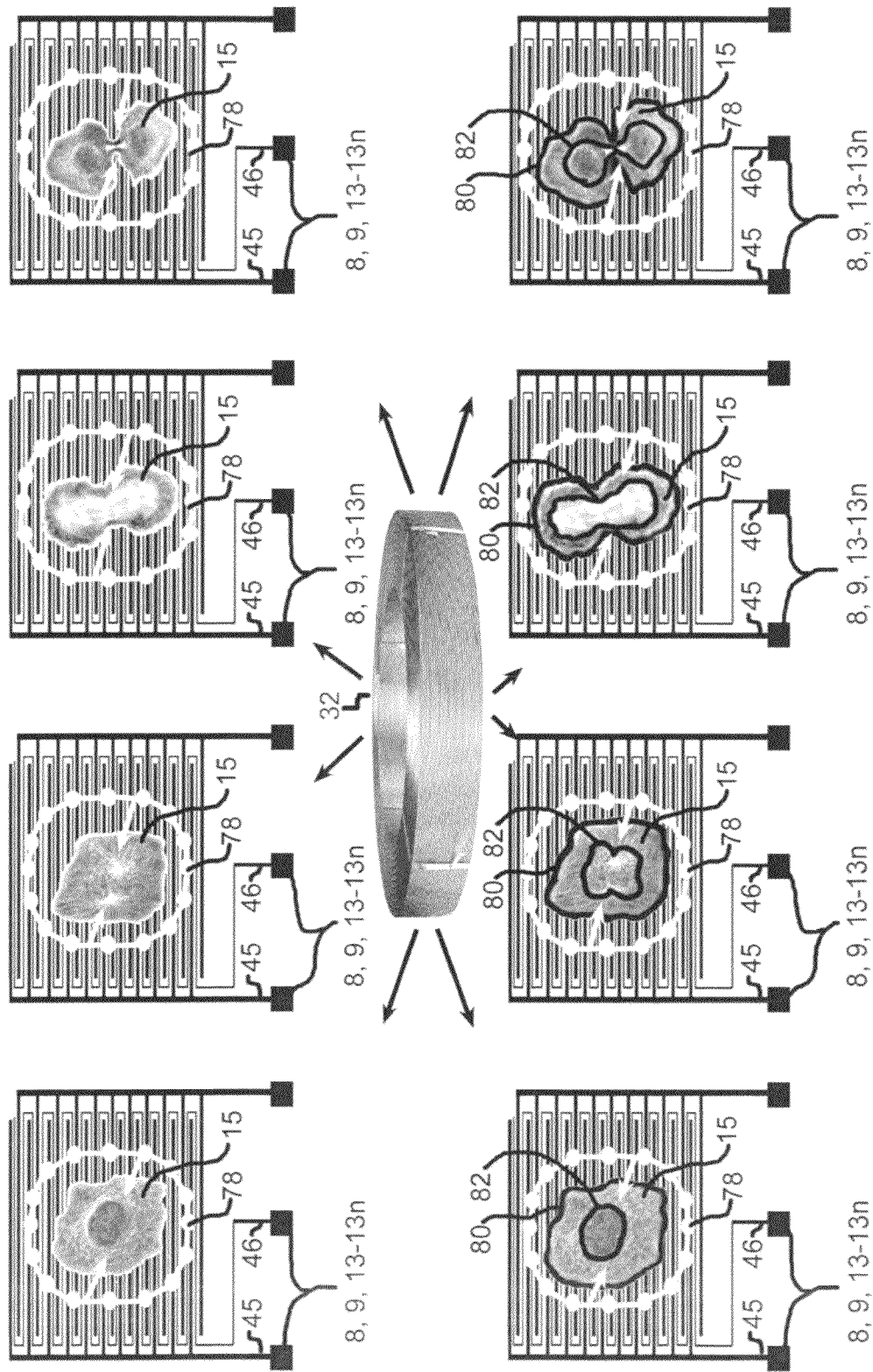
FIG. 6A is a series of simulated accelerated cell changes with cell perimeter and detail mapping as well as cell uptake of a chemical compound per the present invention.

Referring now to FIG. 6A, a catalytic bioavailable media 78 which may include a drug, a vitamin, or a mineral compound, in conjunction with a resonant frequency 8, individually or combined with a waveform 9 and a harmonic 13 through 13n combinations may be applied to a cell 15 through traces 45 and 46 and/or electromagnetic transducer 32 to stimulate a cellular behavior alteration 69 in the form of simulated accelerated mitosis as seen in the series of cell 15 changes illustrated in the top row. In the bottom row of FIG. 6A, said cellular behavior alteration 69 may be mapped (by software program 63 in response to image data derived from camera 58 as detailed in FIG. 1) as black outline 80 around the perimeter of cell 15 and black outline 82 around the nucleus 83 of a cell 15. The black arrows indicate electromagnetic waves radiating from electromagnetic transducer 32.

Many of the elements and software capabilities included in the present invention are available in various industries and disciplines so they are not detailed herein beyond the description presented. However, the present invention is a unique and novel system and apparatus combination that incorporates methods, features, and components not found in any other single apparatus or toolset.

It is to be understood that the embodiments and variations shown and described herein are merely illustrative of the principles of this invention and that various modifications may be implemented by those skilled in the art without departing from the scope and spirit of the invention.

I claim:

1. An electro medical, tool optimizing system comprising: at least one light source, said at least one light source configured to impart at least one wavelength of light to at least one biological cell; at least one biological cell magnification device; at least one imaging device configured to detect at least one biological cell; at least one waveform generator configured to output at least one waveform or pulse; said at least one waveform generator electrically coupled to at least one energy radiating transducer and at least one first direct contact electrical connection configured to apply said at least one waveform or pulse to at least one biological cell behaving in a first viable state; at least one energy sensing transducer or at least one second direct contact electrical connection configured to sense electrical energy emanating from at least one biological cell behaving in said first viable state; at least one computer electrically coupled to said at least one light source, said at least one biological cell magnification device, said at least one imaging device, said at least one waveform generator, and said at least one energy sensing transducer or said at least one second direct contact electrical connection; wherein said at least one computer modifies said at least one waveform or pulse so that said at least one biological cell behaves in at least one second viable state, said at/east one second viable state is selected from one or more of the group consisting of: cellular division, a change in immune system response, a change in metabolism, a change in DNA or RNA replication, a change in transcription, a change in translation, a change in cell signaling, a change in cell surface activity, a change in cell surface permeability, reactivation of stem cell functionality in adult differentiated cells, alteration of electrical conductivity or alteration of electrical conductivity in an ambient medium surrounding said at least one biological cell, and altered uptake of drugs, vitamin or mineral compounds by said at least one biological cell.

2. The electro medical tool optimization system according to claim 1, wherein said at least one waveform or said at least one pulse is selected from the group consisting of one or more of: at least one waveform detected from said at least one biological cell, direct current, a fraction of a single hertz, acoustic, ultrasonic, radio frequency, microwave, millimeter wave, and other electromagnetic spectra.

3. The electro medical tool optimization system according to claim 1, wherein said at least one energy radiating transducer is selected from the group consisting of: a coil, an antenna, an ultrasonic transducer, a waveguide, a horn, or any other device able to transmit electrical or electromagnetic energy.

4. The electro medical tool optimization system according to claim 1, wherein said at least one energy sensing transducer is selected from the group consisting of: a coil, an antenna, an ultrasonic transducer, a waveguide, a horn, or any other device able to receive electrical or electromagnetic energy.

5. The electro medical tool optimization system according to claim 1, wherein said at least one computer incorporates at least one software database populated with said at least one biological cell first viable state data that is compared to said at least one biological cell second viable state data wherein said comparison of said at least one biological cell first viable state data and said at least one biological cell second viable state data is used to modify said waveform or pulse.

6. The electro medical tool optimization system according to claim 1 configured to apply at least one waveform sweep to said at least one biological cell;
   wherein said at least one waveform sweep includes at least one waveform or at least one pulse selected from the group consisting of one or more of: at least one waveform detected from said at least one biological cell, direct current, a fraction of a single hertz, acoustic, ultrasonic, radio frequency, microwave, millimeter wave, and other electromagnetic spectra.

7. The electro medical tool optimization system according to claim 1, wherein said at least one waveform or said at least one pulse is further modified with harmonics, frequency, phase, or amplitude shifts.

8. The electro medical tool optimization system according to claim 1 which includes at least one visual display configured to present to an operator a representation of said electrical, acoustic, or electromagnetic energy radiating toward or being applied to, or emanating from said at least one biological cell behaving in said first viable state or said second viable state, and a representation of said at least one biological cell behaving in said first viable state or said second viable state.

9. The electro medical tool optimization system according to claim 1, wherein said at least one biological cell magnification device is a microscope.

10. The electro medical tool optimization system according to claim 1 which includes at least one operator interface.

11. An electro medical tool optimizing system comprising: at least one light source, said at least one light source configured to impart at least one wavelength of light to at least one biological cell; at/east one biological cell magnification device; at least one imaging device configured to detect said at least one biological cell; at least one waveform generator configured to output at least one waveform or pulse; said at least one waveform generator electrically coupled to at least one energy radiating transducer and at least one first direct contact electrical connection configured to apply said at least one waveform or pulse to said at least one biological cell behaving in a first viable state; at least one operator interface electrically coupled to said at least one waveform generator; at least one energy sensing transducer or at least one second direct contact electrical connection configured to sense electrical energy emanating from said at least one biological cell behaving in said first viable state; at least one visual display configured to present to an operator a representation of said at least one biological cell; and at least one visual display configured to present to an operator a representation of said electrical, acoustic, or electromagnetic energy radiating toward or being applied to, or emanating from said at least one biological cell behaving in said first viable state;
wherein an operator may modify said at least one waveform or said at least one pulse so that said at least one biological cell behaves in at least one second viable state, said at least one second viable state is selected from one or more of the group consisting of: altered cellular division, a change in immune system response, a change in metabolism, a change in DNA or RNA replication, a change in transcription, a change in translation, a change in cell signaling, a change in cell surface activity, a change in cell surface permeability, reactivation of stem cell functionality in adult differentiated cells, alteration of electrical conductivity or alteration of electrical conductivity in an ambient medium surrounding said at least one biological cell, and altered uptake of drugs, vitamin or mineral compounds by said at least one biological cell.

12. The electro medical tool optimization system according to claim 11, wherein said at least one waveform or said at least one pulse is selected from one or more of the group consisting of: at least one waveform detected from said at least one biological cell, direct current, a fraction of a single hertz, acoustic, ultrasonic, radio frequency, microwave, millimeter wave, and other electromagnetic spectra.

13. The electro medical tool optimization system according to claim 11, wherein said at least one biological cell magnification device is a microscope.

14. The electro medical tool optimization system according to claim 11, wherein said at least one energy radiating transducer is selected from one or more of the group consisting of: a coil, an antenna, an ultrasonic transducer, a waveguide, a horn, or any other device able to transmit electrical or electromagnetic energy.

15. The electro medical tool optimization system according to claim 11, wherein said at least one energy sensing transducer is selected from one or more of the group consisting of: a coil, an antenna, an ultrasonic transducer, a waveguide, a horn, or any other device able to receive electrical or electromagnetic energy.

16. The electro medical tool optimization system according to claim 11, wherein said at least one waveform or said at least one pulse can be further modified with harmonics, frequency, phase, or amplitude shifts.

\* \* \* \* \*